(12) United States Patent
Kapellen et al.

(10) Patent No.: US 9,371,300 B2
(45) Date of Patent: Jun. 21, 2016

(54) CATALYTIC EPOXIDATION PROCESS

(71) Applicant: Evonik Degussa GmbH, Essen (DE)

(72) Inventors: Mark Kapellen, Ottignies Louvain-la-Neuve (BE); Joachim Lienke, Schiedam (NL); Jimmy Antonius Van Rijn, Ottignies Louvain-la-Neuve (BE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/434,609

(22) PCT Filed: Oct. 7, 2013

(86) PCT No.: PCT/EP2013/003018
§ 371 (c)(1),
(2) Date: Apr. 9, 2015

(87) PCT Pub. No.: WO2014/056603
PCT Pub. Date: Apr. 17, 2014

(65) Prior Publication Data
US 2015/0274683 A1    Oct. 1, 2015

(30) Foreign Application Priority Data
Oct. 9, 2012    (EP) .................................... 12075116

(51) Int. Cl.
| C07D 303/00 | (2006.01) |
| C07D 301/12 | (2006.01) |
| B01J 31/18 | (2006.01) |
| B01J 31/26 | (2006.01) |
| C07D 301/36 | (2006.01) |

(52) U.S. Cl.
CPC ............. *C07D 301/12* (2013.01); *B01J 31/182* (2013.01); *B01J 31/26* (2013.01); *C07D 301/36* (2013.01); *B01J 2231/72* (2013.01); *B01J 2531/72* (2013.01)

(58) Field of Classification Search
CPC ... C07D 301/12; C07D 301/36; B01J 31/182; B01J 31/26; B01J 2531/72; B01J 2231/72
USPC ......................................................... 549/513
See application file for complete search history.

(56) References Cited

U.S. PATENT DOCUMENTS 6,673,950 B1 *  1/2004  Teles et al. .................... 549/529
8,729,282 B2    5/2014  Postma et al.
(Continued)

FOREIGN PATENT DOCUMENTS

EP    1403219    3/2004

OTHER PUBLICATIONS

International Search Report for PCT/EP2013/003018 filed Oct. 7, 2013.
Written Opinion of the International Searching Authority for PCT/EP2013/003018 filed Oct. 7, 2013.
(Continued)

*Primary Examiner* — T. Victor Oh
(74) *Attorney, Agent, or Firm* — Law Office of: Michael A. Sanzo, LLC

(57) ABSTRACT

Methods and compositions are provided for the manufacture of an epoxide. In one embodiment, the invention provides a process for the manufacture of an epoxide including providing an olefin, an oxidant, alkaline earth metal ions, a catalyst component, a buffer component, and water to form a reaction mixture and reacting the olefin with the oxidant in the reaction mixture.

20 Claims, 1 Drawing Sheet

(56) References Cited

U.S. PATENT DOCUMENTS

| | | |
|---|---|---|
| 8,802,873 B2 | 8/2014 | Postma et al. |
| 9,024,048 B2 | 5/2015 | Kapellen et al. |
| 2011/0137054 A1* | 6/2011 | Postma et al. ............... 549/531 |
| 2011/0137055 A1 | 6/2011 | Postma et al. |
| 2012/0289722 A1 | 11/2012 | Muppa et al. |
| 2014/0113801 A1 | 4/2014 | Kapellen et al. |
| 2014/0296545 A1 | 10/2014 | Postma et al. |

OTHER PUBLICATIONS

International Preliminary Report on Patentability for PCT/EP2013/003018 filed Oct. 7, 2013.

De Vos, et al., "Epoxidation of Terminal or Electron-deficient Olefins with H2O2, catalysed by Mn-trimethyltriazacyclonane Complexes in the Presence of an Oxalate Buffer," *Tetrahedron Letters* 39(20):3221-3224 (May 1998).

* cited by examiner

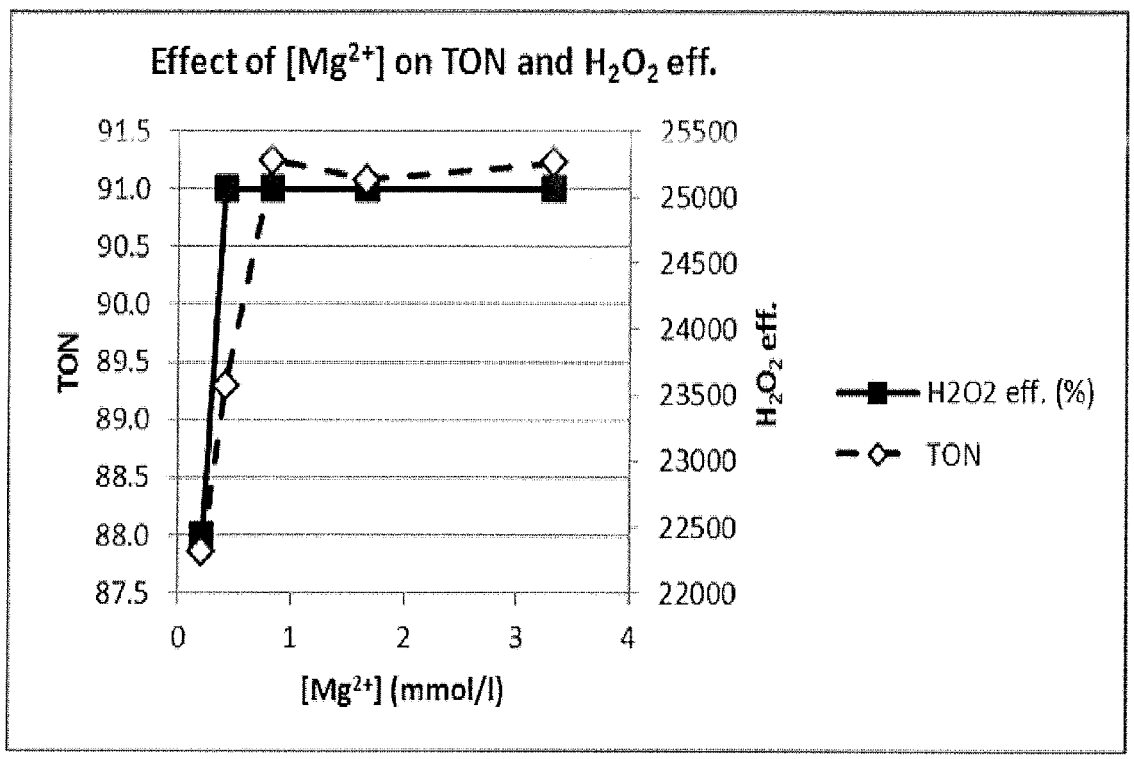

CATALYTIC EPOXIDATION PROCESS

RELATED APPLICATION DATA

This application claims the benefit of PCT Application PCT/EP2013/003018 with an International Filing Date of Oct. 7, 2013, published as WO 2014/056603 A2, which further claims priority to European Patent Application No. EP 12075116.9 filed Oct. 9, 2012, the entire contents which are hereby incorporated by reference.

FIELD OF THE INVENTION

The invention relates to catalytic oxidation processes, and in particular, to catalytic epoxidation processes.

BACKGROUND OF THE INVENTION

A process for the manufacture of a 1,2-epoxide is described in the published European patent application EP 2149569. The publication describes the catalytic oxidation of an olefin using a water soluble manganese complex as the oxidation catalyst and hydrogen peroxide as the oxidant. The process described is carried out in a multiphasic system, such as a biphasic system, having an organic phase, which may be a liquid phase or a gaseous phase, and an aqueous phase. For this reason, the 1,2-epoxide is produced with a desirable selectivity towards the 1,2-epoxide, while providing an improved ease of isolating the produced 1,2-epoxide.

However, while the epoxide product is produced at a desirable selectivity and is easily separated, the economics of this process depend on both the efficiency of the catalyst described by the turnover number (TON) and the efficiency of the oxidant utilization described as yield.

Therefore, there is a need for a process and composition for improving the oxidant efficiency and TON of a catalytic oxidation process.

SUMMARY OF THE INVENTION

Accordingly, the invention provides for catalytic epoxidation processes in the presence of a catalyst and an additive.

In one embodiment, the invention provides a process for the manufacture of an epoxide including providing components to form a reaction mixture, wherein the components comprise an olefin, an oxidant, alkaline earth metal ions, a catalyst component, a buffer component, and water, and reacting the olefin with the oxidant in reaction mixture.

DETAILED DESCRIPTION OF THE FIGURES

The following is a brief description of figures.

FIG. 1 illustrates a graph of results of turn over number (TON) and hydrogen peroxide efficiency ($H_2O_2$ eff. (%)) versus the concentration of additive magnesium ($Mg^{2+}$) ions from one embodiment of the process described herein.

DETAILED DESCRIPTION OF THE INVENTION

As used in the current specification, the terms "epoxidation" and "oxidation" refer to the same reaction; the conversion of the carbon-carbon double bond of an olefin, into an oxirane ring. The invention is hereafter discussed in greater detail. Chemical compounds having an oxirane ring are described herein as epoxide compounds.

The following description refers to Turn Over Number (TON). As described herein the Turn Over Number refers to the number of moles of substrate that a mole of catalyst can convert before becoming deactivated.

As described herein, oxidant efficiency, such as hydrogen peroxide efficiency, is defined herein as ratio of moles of epoxide formed divided by the moles of oxidant consumed, in particular the ratio of moles epoxide formed divided by the moles of hydrogen peroxide consumed.

The invention provides for epoxidation of an olefin, in the presence of a catalyst and an additive of alkaline earth metal ions. It was surprisingly and unexpectedly discovered that the presence of the alkaline earth metal ions improved both the Turn Over Number (TON) and increased the oxidant conversion efficiency over the use of demineralized (demi) water. This surprising and unexpected discovery was found to even occur in the presence of other metal ions, such as alkali metal ions introduced as a buffer component into the reaction mixture.

In one embodiment of the catalytic oxidation process described herein, the process includes reacting an olefin with an oxidant in the presence of a catalyst, alkaline earth metal ions, and a buffer component, in an aqueous medium at acidic conditions.

The alkaline earth metal ions, Group II (Group 2) of the Periodic Table of the Elements, may include magnesium ions, calcium ions, strontium ions, barium ions, and combinations thereof. The alkaline earth metal ions have a 2+ oxidation state.

The metal ions may be provided from a metal ion source including alkaline earth metal salts, an ion containing aqueous solution, and combinations thereof. Metal ions are preferably provided as metal ions from an alkaline earth metal salt of an acid having a pKa of 15 or less, such as a pKa from −10 to 15, for example, a pKa from −9 to about 14 Examples of acids having a pKa of 15 or less include inorganic acids, such as hydrochloric acid, sulfuric acid, nitric acid, phosphoric acid, carbonic acid, and combinations thereof, organic acids, such as acetic acid, oxalic acid, and combinations thereof, and combinations of the inorganic and organic acids. Non-limiting examples of suitable alkaline earth metal salts include magnesium chloride, magnesium sulfate, magnesium nitrate, magnesium acetate, magnesium carbonate, magnesium hydrogencarbonate, magnesium phosphate, magnesium oxalate, calcium chloride, calcium nitrate, calcium acetate, calcium hydrogen carbonate, strontium chloride, strontium nitrate, barium chloride, barium nitrate and combinations thereof.

The ion containing aqueous solution may comprise mineral water, or processed water provided by a water utility company or government agency, for example, "tap" water, which may also be referred to as utility water. The ion containing aqueous solution may comprise a natural water source that contains alkaline earth metal ions, such as magnesium or calcium ions, as part of the natural hardness.

The alkaline earth metal ions may be present in an amount from about 0.125 millimoles per liter (mmol/l) to about 8 mmol/l of the composition, such as from about 0.25 mmol/l to about 4 mmol/l. For ion containing aqueous solutions, the ion concentration may be described in view of water hardness, for example, having a water hardness from about 1° degree of General Hardness (dH) to about 40° dH, where one degree of dH correspond to about 0.178 mmol/l divalent ions in the water, such that from about 1° dH to about 40° dH corresponds to an amount from about 0.178 mmol/l to about 7.12 mmol/l.

Alternatively, the alkaline earth metal ions, for example, magnesium and calcium metal ions, when present, the alkaline earth metal ions may be present in an amount up to about 715 ppm, such as from about 5 ppm to about 160 ppm of the composition, for example from about 10 to about 80 ppm.

Without being bound to any theory, it is believed that the presence of alkaline earth metal ions stabilizes the hydrogen peroxide and suppresses its disproportionation. It is believed that the increased TON is a secondary effect resulting from the suppressed decomposition. While magnesium has been observed to have potentially stabilizing effects in other technical fields, such as paper bleaching, it was surprisingly and unexpectedly discovered by the inventors that the stabilizing effect is found in epoxidation reactions and in acidic conditions. Furthermore the stabilizing effect of magnesium is observed in the absence of any precipitation or solid substrate surfaces, and in the absence of metal ions such as copper and iron that are known to destabilize hydrogen peroxide.

The epoxidation process may be carried out in a reaction mixture having a single phase or multiphasic system, such as a biphasic system, having at least an aqueous phase. The aqueous phase may be essentially a 100% water phase excluding any olefins and/or the corresponding oxides dissolved therein formed during the catalytic oxidation reaction. The reaction mixture may be free of organic solvents. Alternatively, the reaction mixture may be free of organic solvents, excluding any olefins and/or the corresponding oxides dissolved therein formed during the catalytic oxidation reaction.

The process may be performed in a multi-phasic system. The multiphasic system may be created by adding the olefin, for example, allyl chloride or allyl acetate, with limited solubility to an aqueous phase in an amount greater than what dissolves in the aqueous phase. Suitable substrate may have a maximum solubility of about 100 g/L (at 20° C.), such as from 0.01 g/L to 100 g/L at 20° C. The phase ratio by volume of the two phases may be a volume ratio of organic to aqueous phase from about 5:1 to 1:10, such as from about 1:1 to about 1:2. The organic phase may be distributed in the aqueous phase through a process such as agitation.

In an alternative embodiment, the epoxidation processes may be performed with organic solvents in the aqueous phase. The current epoxidation process may be carried out in an aqueous reaction medium comprising 10 volume percent or less of co-solvents. The use of organic co-solvents, such as water-soluble alcohols, is believed to improve the solubility of the olefin. Examples of suitable co-solvents include, for example, acetone, acetonitrile, methanol, tetra hydrofuran (THF), and combinations thereof. The amount of organic co-solvents may be reduced to a minimum and the reaction may be carried out in a reaction medium substantially composed of water. With the exclusion of the presence of the reactants and the epoxidation products, the aqueous reaction medium therefore suitably comprises at least 90% by volume of water (v %), such as at least 95 v %, for example, at least 99 v %, and in some embodiments, at least 99.9 v % of water.

According to the invention, the olefin may be functionalized. The olefin may be a liquid under process conditions, for example, allyl chloride or liquefied propylene, but also a gas, for example, gaseous propylene.

Suitable olefins include, in one embodiment, olefins having at least one unsaturated —C=C— bond, such as at least one unsaturated —C=CH$_2$ group. The olefin may comprise more than one unsaturated —C=C— bond. Moreover, the unsaturated —C=C— bond need not be a terminal group. Terminally olefins may have one or more terminal —C=CH$_2$ bonds.

Suitable examples of terminal olefins include the following compounds:
R—CH=CH$_2$;
R'—(CH=CH$_2$)$_n$;
R—CH$_2$—CH=CH$_2$;
X—CH$_2$—CH=CH$_2$;
X—CH=CH$_2$;
Y—(CH=CH$_2$)$_2$; and combinations thereof, wherein R is a radical of 1 or more carbon atoms optionally comprising 1 or more heteroatoms (such as oxygen, nitrogen or silicon); R' is a multivalent radical of 1 or more carbon atoms optionally comprising 1 or more heteroatoms wherein n corresponds with the valence of the multivalent radical; X is a halogen atom, and Y is an oxygen atom.

Of particular interest are olefins selected from the compounds allyl halides, such as allyl chloride; 1-alkenes, such as propene and butadiene; a cycloalkene, including aromatic compounds; mono-, di- or polyallyl ethers of mono-, di- or polyols and phenols; allylesters such as allylacetate and esters of linear or branched aliphatic carbonic acids, allylalcohol, mono-, di- or polyallyl esters of mono-, di- or polyacid; and combinations thereof. Examples of suitable olefins include vinyl chloride, allyl chloride, allyl acetate, propene, butadiene, and combinations thereof.

In another embodiment of the present invention, the olefin is selected from allyl bromide, allyl chloride and allyl acetate. In another embodiment of the invention allyl chloride is used for the manufacture of epichlorohydrin, because of the commercial interest and ease of isolating the produced epichlorohydrin. According to another embodiment of the present invention the olefin is propylene in order to produce propylene oxide.

It has been observed that improved epoxide product conversion rates may be achieved by the use of olefins that have limited solubility in water, for example, allyl chloride and allyl acetate instead of conventionally used allyl alcohol. The multiphasic system may be created by adding the olefin with limited solubility to an aqueous phase in an amount greater than what dissolves in the aqueous phase. Suitable olefins may have a maximum solubility of about 100 g/L (at 20° C.), such as from 0.01 g/L to 100 g/L at 20° C.

The epoxidation process may use oxidants including oxygen-containing gases, inorganic peroxides, organic peroxides, peracids, permanganates, hydrogen peroxide precursors, and combinations thereof. The oxidant may be provided at a concentration from about 0.05 wt. % to about 4 wt. %, such as from about 0.1 wt. % to about 3 wt. %, for example, from about 0.3 wt. % to about 2 wt. % of the composition. Suitable oxygen-containing gases include oxygen gas (O$_2$), atmospheric air, and combinations thereof. Suitable inorganic peroxides include, for example, hydrogen peroxide, sodium peroxide, urea hydroperoxide, and combinations thereof. Hydrogen peroxide may also be generated in situ by appropriate techniques known in the art. Hydrogen peroxide precursors may include processes using metal to form hydrogen peroxide from hydrogen gas and oxygen gas.

Hydrogen peroxide may be used in an aqueous solution at a concentration that may vary, from 15% to 98% (propellant grade), such as industrial grades varying from 20 to 80%, for example, from 30 to 70%.

The catalyst component may be a complex having at least one metal atom selected from the group consisting of manganese, iron, cobalt, titanium, vanadium, tungsten, molybdenum, and combinations thereof.

One suitable catalyst component is a manganese complex which may be one or more compounds selected from the group of a mononuclear species, a binuclear species, a polynuclear species, or combinations thereof. The specie may include:

a mononuclear species of the general formula (I):

$$[LMnX_m]Y \qquad (I);$$

a binuclear species of the general formula (II):

$$[LMn(\mu-X)_m MnL]Y_n \qquad (II), or$$

a polynuclear species of the general formula (III):

$$[L_n Mn_n(\mu-X)_m]Y_n \qquad (III),$$ and a combination of the complexes, where Mn is a manganese atom; L or each L is independently a polydentate ligand. Each X is independently a coordinating species and each μ-X is independently a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, $C_2O_4^{2-}$, and $SO_4^{2-}$ and combinations thereof, wherein R is a $C_1$-$C_{20}$ radical selected from the group consisting of alkyl, cycloalkyl, aryl, benzyl and combinations thereof. The manganese constituent may be in the oxidation states of +2, +3, +4, or +7. In the formulas, m may be from 1 to 3, for example 3, and n may be from 0 to 3, such as 1 or 2. Y is a non-coordinating counter ion. The non-coordinating counter ion Y may provide for the charge neutrality of the complex and the value of n depends upon the charge of the cationic complex and anionic counter ion Y. Counter ion Y may for instance be an anion selected from the group consisting of $RO^-$, $Cl^-$, $Br^-$, $I^-$, $F^-$, $SO_4^{2-}$, $RCOO^-$, $PF_6^-$, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. In one embodiment, an ion of $CH_3COO^-$ or $PF_6^-$ may be used as the non-coordinating counter ion.

Suitable polydentate ligands include acyclic compounds containing at least 7 atoms in the backbone or cyclic compounds containing at least 9 atoms in the ring, each having the nitrogen atoms separated by at least two carbon atoms. A suitable class of ligands include 1,4,7-triazacyclononane ("Tacn") and substituted versions thereof. The substituted 1,4,7-triazacyclononane compound may be substituted with one or more organic groups having a $C_1$ to $C_{20}$ organic group selected from the group consisting of alkyl, cycloalkyl, aryl, and combination thereof. For example, 1,4,7-triazacyclononane, may be substituted by one or more methyl groups, to form N',N'',N'''-trimethyl-1,4,7-triazacyclononane (TmTacn). Examples of suitable ligands include compounds selected from the group of N',N'',N'''-trimethyl-1,4,7-triazacyclononane, 1,5,9-trimethyl-1,5,9-triazacyclododecane (1,5,9-$Me_3$TACD), 2-methyl-1,4,7-trimethyl-1,4,7-triazacyclononane (2-Me, 1,4,7-$Me_3$TACN), 2-metyl-1,4,7-triazacyclononane, and combinations thereof.

In one embodiment of the manganese complex, the manganese complexes are those of the formula $[Mn^{IV}_2(\mu-O)_3L_2](Y)_n$ (same as formula: $[LMn(\mu-O)_3MnL](Y)_n$), wherein n is 2, and L and Y have the meaning identified above, such as TmTacn as ligand, and $PF_6^-$ or acetate ($CH_3CO_2^-$, hereinafter OAc) as counterion. The catalyst component system comprising a water soluble manganese complex is described above. One complex for the current invention comprises 1,4,7-trimethyl-1,4,7,-triazacyclononane ("TmTacn") as the ligand or ligands.

Additionally, the catalyst component may be formed in situ from the reaction of a free ligand and a source of the metal ion, in particular manganese. The free ligand may be the ligand described herein. The metal ion source may comprise any metal salt of inorganic acids, organic acids or combinations thereof. Particular examples of suitable manganese salts include salts selected from the group consisting of manganese sulfate, manganese acetate, manganese nitrate, manganese chloride, manganese bromide, and combinations thereof in the oxidation state (II) and (III). The manganese source may be provided as a solid or in a solution.

The manganese complex is used in catalytically effective amounts. The catalyst component may be used in a molar ratio of catalyst component (Mn) to the oxidant of from 1:10 to 1:10,000,000, such as from 1:100 to 1:1,000,000, for example, from 1:200 to 1:100,000. As a matter of convenience the amount of catalyst component may also be expressed in terms of its concentration, when keeping in mind the volume of the aqueous medium. For instance, it may be used in a molar concentration (based on the Mn) of from about 0.001 to about 10 mmol/L, such as from about 0.002 to about 2 mmol/L and for example, from about 0.005 to about 1 mmol/L.

The olefin and the oxidant may be provided for the epoxidation reaction at a molar ratio of olefin to oxidant that may be greater than 1:2, such as about 1:1 or greater, for example, about 12:1. This ratio may be in the range of from about 1:2 to about 12:1, such as from about 1:1 to about 12:1. For example, in different process embodiments, the molar ratio of olefin to oxidant may be about 1:1.2, about 1:1, about 1.2:1, about 2:1, or about 4:1, or in the range of 2:1 to 12:1. For example, in some continuous processes embodiments, the olefin to oxidant molar ratio may be about 1:1 To ensure optimal peroxide efficiency, the oxidant may be added to the aqueous phase at a rate about equal to the reaction rate of the catalytic oxidation.

The manganese complex may be used with the components for an epoxidation reaction as described herein to produce an epoxide product. The epoxidation process includes reacting an olefin with an oxidant in the presence of a manganese complex as a catalyst component and alkaline earth metal ions, with an optional buffer component, in an aqueous medium at acidic conditions. The manganese complex of the epoxidation reaction may have a catalytic activity, as measured by Turn Over Frequency, from $1\ s^{-1}$ to $2500\ s^{-1}$, such as from about $5\ s^{-1}$ to $500\ s^{-1}$ depending on process conditions.

The epoxidation reaction may occur under acidic conditions, whereby, the reaction mixture may have a pH from about 1 to less than 7, such as from about 2 to less than 6, for example from about 3 to about 5. The pH is therefore (well) below that used when bleaching olefins with hydrogen peroxide as the oxidant, typically carried out at alkaline conditions.

Optionally, to provide a desired reaction mixture pH or a post-reaction product pH, a pH adjusting agent may be added. The pH adjusting agent may be an inorganic base, an organic base, or combinations thereof. The pH adjusting agent may have a cation oxidation state different than two (2+), such as one (1+). Examples of suitable bases include compounds selected from the group of sodium hydroxide (NaOH), potassium hydroxide (KOH), ammonium hydroxide ($NH_4OH$), aliphatic amines, potassium carbonate, sodium carbonate, potassium oxalate, sodium oxalate, and combinations thereof. The pH adjusting agent has a cation oxidation state different than two (2+), such as one (1+).

The reaction mixture may further comprise a buffer component to stabilize the pH in a certain range. While the following component is referred to as a buffer component, the component may also function or be utilized as a co-catalyst, a bridging ion, and/or a co-ligand, as described herein for the respective components. The buffer component may be used in a molar ratio to the catalyst in the range from about 1:1 to about 17,000:1, such as from about 1:10 to about 1:1000. In some embodiments, the concentration of the buffer component in the aqueous phase may range from about 0.05 wt % to about 9 wt %, such as from about 0.1 wt % to about 1 wt %. According to still another embodiment of the invention, the buffer component, if any, and oxidation catalyst are fed as a pre-mixed mixture.

The buffer component, or co-catalyst, may comprise an acid, an acid salt, or combination thereof, such as an organic acid and its conjugated base, an acid-salt combination.

Suitable acids include with aliphatic or aromatic organic acids, such as oxalic acid, acetic acid, glycolic acid, tartaric acid, malonic acid, succinic acid, citric acid and aromatic acids based on substituted benzoic acids, and combinations thereof; inorganic acids, such as phosphoric acid, and combinations thereof.

Suitable salts include the alkaline metal salts of the above mentioned acids, such as alkaline metal salts of oxalate salt, citrate salts, malonate salt, succinate salt, glutarate salt, acetate salt, benzoic salts, phosphate salts, butanoate salts, and combinations thereof among others. Examples of suitable salts include sodium oxalate, sodium citrate, disodium phosphate-monosodium phosphate, 4-chlorobutanoate, benzoic salt and combinations thereof. In one embodiment, the cations of the salts have an oxidation state of 1+, or alternatively, the cations of the salt have an oxidation state different than 2+.

Suitable acid-salt combinations may be selected from the group of oxalic acid-sodium or potassium oxalate salt, hydrochloric acid-sodium or potassium citrate, malonic acid-sodium or potassium malonate salt, succinic acid-sodium or potassium succinate, glutaric acid-sodium or potassium glutrate, acetic acid-sodium or potassium acetate salt, citric acid-sodium or potassium citrate salt, disodium phosphate-monosodium phosphate, 4-chlorobutanoic acid-4-chlorobutanoate, ortho-chloro benzoic acid-sodium or potassium ortho-chloro benzoic salt, para-chloro benzoic acid-sodium or potassium para-chloro benzoic salt, ortho-fluoro benzoic acid-sodium or potassium ortho-fluoro benzoic salt, para-fluoro benzoic acid-sodium or potassium para-fluoro benzoic acid salt, and combinations thereof.

The aqueous phase may further comprise a phase transfer agent and/or a surfactant. The phase transfer agent and/or a surfactant may be used if an olefin has low solubility (for example, below 0.1 g/L water). Phase transfer agents that may be used in the process of the invention include quaternary alkyl ammonium salts. Surfactants that may be used in the process of the invention include non ionic surfactants such as Triton X100™ available from Union Carbide.

Depending on the reactants and reaction type, the epoxidation process may be carried out at a temperature in the range from about 0° C. to about 70° C., such as from about 4° C. to about 45° C., for example, from about 5° C. to about 40° C. Moreover, the process may be carried out at reduced pressure or under increased pressure, such as from 0.1 bars to 20 bars, such as from 0.9 bars to 9 bars. For instance, a higher pressure may be used when propylene is epoxidized.

The epoxidation reaction may be further performed under agitation or mixing conditions. For example, the epoxidation reaction may be performed in a reactor having a stirring disposed therein or in a loop reactor having a mixing component disposed before and/or within the loop reactor lines. The amount of agitation will vary based on the epoxidation process, and the invention contemplates that sufficient agitation is performed to provide for performing the process as described herein to provide results as described herein.

The reactor according to the invention further comprises dispersing means for dispersing the organic olefin phase into the aqueous phase and cooling means for controlling the temperature of the catalytic oxidation, because of its exothermic nature.

The epoxidation process may be a batch process, a semi-batch process, or a continuous process. Suitable reactors include reactors for batch processes, semi-batch processes, and/or continuous processes, and may include, for example, a plug flow reactor (PFR), a continuous stirred tank reactor (CSTR), and a loop reactor among others.

In operation, the apparatus may be used as follows with the process described herein. While the following description illustrates the epoxidation of an allyl chloride, the invention contemplates that the process and any of the components described herein may be used in the apparatus described herein.

Initially, the olefin, such as allyl chloride, the oxidant, such as hydrogen peroxide, the additive of alkaline earth metal ions, and catalyst component, such as the manganese complex as described herein are charged with water to a reactor. A co-catalyst component, such as oxalic acid, or a buffer component of oxalic acid/sodium oxalate salt, may also be charged into the reactor. The components may be introduced simultaneously, periodically or sequentially into the reactor. The components are allowed to react and produce an epoxide component in a reaction mixture, such as epichlorohydrin from allyl chloride, as described herein. The reaction mixture may be multiphasic, such as at least one organic phase and one aqueous phase. The epoxide component will separate out into at least one of the organic phases. It is believed that is some embodiments, the organic precursor material, such as epichlorohydrin may form a second and separate organic phase from the epoxide containing organic phase.

The following experiments illustrate the processes for the manganese complex and additives as described herein.

EXAMPLES

Experimental set up. The experiments were carried out in a jacketed glass batch reactor on 200 ml scale with temperature control, pH control, and reflux cooler. The reaction mixture has an initial volume of 200 ml. The reaction mixture includes an organic phase containing the olefin and a water phase containing the catalyst, the additive, and the oxidant, in which the oxidant, such as $H_2O_2$, is fed continuously. The reaction mixture is agitated, such as by stirring, during the experimental process.

The olefin is allyl chloride, the oxidant is hydrogen peroxide, $H_2O_2$, and the catalyst is Dragon Blood A350, a manganese complex, with a buffer component (co-catalyst) of oxalic acid and sodium oxalate. The magnesium ions were added by the addition of magnesium sulfate ($MgSO_4$).

The experiments were performed under two different setups.

In a first setup, the catalyst was used with a variable oxidant feed of $H_2O_2$ aiming at a concentration of about 0.1 wt. %. In the second setup, a constant oxidant feed of $H_2O_2$ was used.

Experiment 1

Effect of Magnesium Added

A process was performed as described above. First, a reference experiment was performed in which the temperature was maintained at 15° C., and the pH controlled at 3.6. To 100 mL of water, 72 mg anhydrous oxalic acid and 164 mg of sodium oxalate was added to form a buffer component solution. A source of alkaline earth metal ions, in the form of solid MgSO$_4$, was added to the aqueous phase after addition of the buffer component. To this buffer component solution, 0.203 mL of 3.5 wt % Dragon A350 (manganese complex) was added and stirred for 5 minutes. To the water phase, 100 mL allyl chloride was added. The allylchloride was dispersed in the water phase for 5 more minutes. Then, at t+=0, hydrogen peroxide was dosed for 210 minutes according to the dosing schedule in Table 1 below. From t=0 to t=210, a 5 wt % oxalic acid solution in water was dosed at a flow rate of 10 mL/h. For pH control, a solution of 0.5 M NaOH was used. In the following description, the abbreviation "mmol/l" is used for millimoles per liter.

TABLE 1

| Time (minutes) | 35 wt % H$_2$O$_2$ (mL/h) |
|---|---|
| 0-15 | 5 |
| 15-20 | 10 |
| 20-25 | 20 |
| 25-35 | 25 |
| 35-45 | 18 |
| 45-60 | 13 |
| 60-85 | 9 |
| 85-150 | 5 |
| 150-180 | 3 |
| 180-210 | 0 |

The H$_2$O$_2$ feed program used for Sample 1 is designated as Reference. When all feed rates of the feed program are increased by, for example, 10%, the H$_2$O$_2$-feed is correspondingly designated as +10% in subsequent tables. Only if the H$_2$O$_2$ feed rate has been constant during the whole experiment, the actual flow rate will be given.

The addition of Mg$^{2+}$ ions has a beneficial effect as shown in Tables 2 and 3. The Mg$^{2+}$ ions were added as solid MgSO$_4$ and were added to the aqueous phase after addition of the buffer component. As can be seen in Table 2, the addition of 1.65 mmol/l (40 ppm) Mg$^{2+}$ ions increases the hydrogen peroxide efficiency from 87 (entry 1) to 96% (entry 2), that is, it decreases the unwanted side reactions from about 13% to about 4%. When the peroxide feed is increased, the TON improves from 20050 to 25130 (entry 3) with a somewhat smaller increase in the efficiency.

TABLE 2

Effect of Mg$^{2+}$ ions

| Entry | Solvent | Exp set up | H$_2$O$_2$-feed | H$_2$O$_2$-eff (%) | TON |
|---|---|---|---|---|---|
| 1 | Demineralized water | Variable H$_2$O$_2$ feed | Reference | 87 | 20050 |
| 2 | Demineralized water + 1.65 mmol/l (40 ppm) Mg$^{2+}$ ions | Variable H$_2$O$_2$ feed | Reference | 96 | 22160 |
| 3 | Demineralized water + 1.65 mmol/l (40 ppm) Mg$^{2+}$ ions | Variable H$_2$O$_2$ feed | +20% | 91 | 25130 |

A preferred Mg$^{2+}$ ions concentration range was determined to be between about 0.40 mmol/l and about 3.30 mmol/l (about 10 and about 80 ppm) as shown in Table 3. The maximum TON was observed if the magnesium concentration exceeded 0.82 mmol/l (20 ppm).

TABLE 3

Effect of Mg$^{2+}$ ions concentration

| Entry | Solvent | Exp set up | H$_2$O$_2$-feed | H$_2$O$_2$-eff (%) | TON |
|---|---|---|---|---|---|
| 1 | Demineralized water + 0.20 mmol/l (5 ppm) Mg$^{2+}$ ions | Variable H$_2$O$_2$ feed | +20% | 88 | 22310 |
| 2 | Demineralized water + 0.41 mmol/l (10 ppm) Mg$^{2+}$ ions | Variable H$_2$O$_2$ feed | +20% | 91 | 23570 |
| 3 | Demineralized water + 0.82 mmol/l (20 ppm) Mg$^{2+}$ ions | Variable H$_2$O$_2$ feed | +20% | 91 | 25280 |
| 4 | Demineralized water + 1.65 mmol/l (40 ppm) Mg$^{2+}$ ions | Variable H$_2$O$_2$ feed | +20% | 91 | 25130 |
| 5 | Demineralized water + 3.30 mmol/l (80 ppm) Mg$^{2+}$ ions | Variable H$_2$O$_2$ feed | +20% | 91 | 25260 |

FIG. 1 is a graph illustrating the effect of [Mg$^{2+}$] (in mmol/l) ions on TON and H$_2$O$_2$-efficiency using the data from Table 3.

Experiment 2

Effect of Drinking Water and Calcium Added

Experiment 2 was performed as shown with Experiment 1 except that Experiment 2 uses a constant hydrogen peroxide feed. Entry 1 of Table 4 shows the results when demineralized water is used. If the demineralized water is replaced with drinking water, Entry 2, both TON and efficiency increases. Finally, addition of calcium to demineralized water improves performance up to a level of drinking water, Entry 3.

TABLE 4

Effect of drinking water and [Ca$^{2+}$]

| Entry | Solvent | H$_2$O$_2$-feed | H$_2$O$_2$-eff (%) | TON |
|---|---|---|---|---|
| 1 | Demineralized water | Constant: 12.5 ml/h | 83 | 22040 |
| 2 | Drinking water containing 1.25 mmol/l (50 ppm) Ca$^{2+}$ ions and 0.33 mmol/l (8 ppm) Mg$^{2+}$ ions (9°dH) | Constant: 12.5 ml/h | 85 | 26270 |
| 3 | Demineralized water containing 1.25 mmol/l (50 ppm) CaCl$_2$ | Constant: 12.5 ml/h | 85 | 26170 |

Experiment 3

Flow Rate

Next, a series of experiments were performed to determine TON and H$_2$O$_2$ efficiency achieved when from about 0.82 mmol/l to about 1.65 mmol/l (about 20 to about 40 ppm) Mg$^{2+}$ ions are added and the feed rate is varied. The results are shown in Table 5 below. It was observed that increasing the feed rate of hydrogen peroxide and thus implicitly increasing the steady state concentration, the TON initially increases, goes via an optimum and decreases when passing the optimum. The H$_2$O$_2$ efficiency, however, decreases with increasing feed rate. TON and efficiency are thus for a certain degree interchangeable. As a consequence, the beneficial effect of this invention can either lead to an increased efficiency, an increased TON or a combination of both depending on the flow rate of peroxide.

TABLE 5

Effect of $H_2O_2$ dosing rate.

| Entry | Solvent | $H_2O_2$-feed | $H_2O_2$-eff (%) | TON |
|---|---|---|---|---|
| 1 | Demineralized water + 1.65 mmol/l (40 ppm) $Mg^{2+}$ ions | Reference | 96 | 22160 |
| 2 | Demineralized water + 0.82 mmol/l (20 ppm) $Mg^{2+}$ ions | +10% | 90 | 23090 |
| 3 | Demineralized water + 0.82 mmol/l (20 ppm) $Mg^{2+}$ ions | +20% | 91 | 25280 |
| 4 | Demineralized water + 0.82 mmol/l (20 ppm) $Mg^{2+}$ ions | +30% | 87 | 23820 |
| 5 | Demineralized water + 1.65 mmol/l (40 ppm) $Mg^{2+}$ ions | +50% | 81 | 23720 |

While the present invention has been described and illustrated by reference to particular embodiments, those of ordinary skill in the art will appreciate that the invention lends itself to variations not necessarily illustrated herein.

We claim:

1. A process for the manufacture of an epoxide, comprising:
providing components to form a reaction mixture, wherein the components comprise:
an olefin;
hydrogen peroxide;
alkaline earth metal ions;
a manganese complex;
a buffer component; and
water; and
reacting the olefin with the hydrogen peroxide in the reaction mixture.

2. The process of claim 1, wherein the alkaline earth metal ions comprise ions selected from the group consisting of magnesium ions, calcium ions, strontium ions, barium ions, and combinations thereof.

3. The process of claim 1, wherein the alkaline earth metal ions are present in the reaction mixture in an amount from about 0.125 mmol/l to about 8 mmol/l.

4. The process of claim 1, wherein the alkaline earth metal ions are provided by an aqueous source.

5. The process of claim 1, wherein the alkaline earth metal ions are provided by a salt selected from the group consisting of magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate, strontium chloride, strontium nitrate, barium chloride, barium nitrate and combinations thereof.

6. The process of claim 4, wherein the aqueous source is selected from the group consisting of mineral water, utility water, and combinations thereof.

7. The process of claim 1, wherein the olefin comprises a terminal olefin selected from the group consisting of: allyl halides; 1-alkenes; mono-, di- and polyallyl ethers of mono-, di- and polyols; allyl alcohol; and mono-, di- and polyallyl esters of mono-, di- and polyacids.

8. The process of claim 7, wherein the terminal olefin is allyl chloride.

9. The process of claim 1, wherein the manganese complex is water-soluble.

10. The process of claim 1, wherein the manganese complex comprises one or more species selected from the group of:
a mononuclear species of the formula (I):

$$[LMnX_m]Y \qquad (I),$$

a binuclear species of the formula (II):

$$[LMn(\mu\text{-}X)_m MnL]Y_n \qquad (II), or$$

a polynuclear species of the formula (III):

$$[L_n Mn_n(\mu\text{-}X)_m]Y_n \qquad (III), and$$

wherein Mn is a manganese atom; L or each L is independently a polydentate ligand, each X is independently a coordinating species and each μ-X is independently a bridging coordinating species, wherein Y is a non-coordinating counter ion and m is from 1 to 4 and n is from 1 to 2.

11. The process of claim 1, wherein the buffer component comprises an organic acid and a salt of the organic acid.

12. The process of claim 11, wherein the salt of the organic acid has a cation having a 1+ oxidation state.

13. The process of claim 1, wherein the components further comprise a pH adjusting agent.

14. The process of claim 1, wherein the reaction mixture comprises acidic conditions.

15. The process of claim 14, where the pH of the reaction mixture is from 2 to less than 7.

16. The process of claim 1, wherein the reaction mixture is free of an organic solvent.

17. The process of claim 1, wherein the alkaline earth metal ions are provided in an amount from about 5 ppm to about 160 ppm.

18. The process of claim 3, wherein the alkaline earth metal ions comprise ions consisting of magnesium ions.

19. The process of claim 18, wherein the magnesium ions are present in the reaction mixture in an amount from about 0.40 mmol/l to about 3.3 mmol/l.

20. The process of claim 19, wherein the reaction mixture is free of an organic solvent.

* * * * *